(12) United States Patent
Peng et al.

(10) Patent No.: US 10,435,376 B2
(45) Date of Patent: Oct. 8, 2019

(54) DERIVATIVES OF 1H-IMIDAZOLE-4,5-DICARBOXAMIDE AND USE THEREOF IN PREPARATION OF ANTICOCCIDIAL DRUGS

(71) Applicant: GUANGZHOU INSIGHTER BIOTECHNOLOGY CO., LTD., Guangzhou (CN)

(72) Inventors: Xianfeng Peng, Guangzhou (CN); Zonghua Qin, Guangzhou (CN)

(73) Assignee: GUANGZHOU INSIGHTER BIOTECHNOLOGY CO., LTD., Guangzhou (CN)

( * ) Notice: Subject to any disclaimer, the term of this patent is extended or adjusted under 35 U.S.C. 154(b) by 55 days.

(21) Appl. No.: 15/777,916

(22) PCT Filed: Nov. 26, 2015

(86) PCT No.: PCT/CN2015/095689
§ 371 (c)(1),
(2) Date: May 22, 2018

(87) PCT Pub. No.: WO2016/141736
PCT Pub. Date: Sep. 15, 2016

(65) Prior Publication Data
US 2018/0370921 A1 Dec. 27, 2018

(30) Foreign Application Priority Data

Mar. 9, 2015 (CN) .......................... 2015 1 0103326

(51) Int. Cl.
C07D 233/90 (2006.01)
C07D 487/04 (2006.01)
A61P 33/00 (2006.01)

(52) U.S. Cl.
CPC ............ C07D 233/90 (2013.01); A61P 33/00 (2018.01); C07D 487/04 (2013.01)

(58) Field of Classification Search
CPC .......................... C07D 487/04; C07D 233/90
USPC ........................................................ 540/502
See application file for complete search history.

(56) References Cited

U.S. PATENT DOCUMENTS 2,872,371 A * 2/1959 Rogers ................ C07D 233/64
514/400
2009/0163545 A1 6/2009 Goldfarb

FOREIGN PATENT DOCUMENTS

CN 104672145 A 6/2015

* cited by examiner

Primary Examiner — Kahsay Habte
(74) Attorney, Agent, or Firm — Gokalp Bayramoglu

(57) ABSTRACT

Disclosed are derivatives of 1H-imidazole-4,5-dicarboxamide and use thereof in preparation of anticoccidial drugs. The derivatives have structural formulae as shown in formulae (I) to (VI). The derivatives of 1H-imidazole-4,5-dicarboxamide as disclosed in the present invention have significant anticoccidial effect, especially against coccidia that show a resistance to other anticoccidial drugs, and thus they can be used in preparation of anticoccidial drug.

9 Claims, No Drawings

DERIVATIVES OF 1H-IMIDAZOLE-4,5-DICARBOXAMIDE AND USE THEREOF IN PREPARATION OF ANTICOCCIDIAL DRUGS

CROSS REFERENCE TO THE RELATED APPLICATIONS

This application is the national phase entry of International Application No. PCT/CN2015/095689, filed on Nov. 26, 2015, which claims priority from Chinese Patent Application 201510103326.1, filed on Mar. 9, 2015, the entire contents of which are incorporated herein by reference.

TECHNICAL FIELD

The present invention relates to the field of Biology, and particularly to a series of derivatives of 1H-imidazole-4,5-dicarboxamide and use thereof in preparation of anticoccidial drugs.

BACKGROUND

Coccidiosis, which is caused by *Eimeria* spp protozoa, is a major animal disease that causes significant losses in the poultry sector. Chicken coccidiosis alone can cause global losses of up to 4 billion US dollars every year. In China, coccidiosis also causes losses of up to 10 billion CNY every year in the poultry sector; in recent years, besides the chicken coccidiosis which has been recognized for a long time, coccidiosis has shown an increasing morbidity in swine and dairy cattle and becomes the major cause of diarrhea and death of suckling and weaned piglets. *Eimeria* spp are protozoan parasites having direct life cycles and their biological characteristics make it difficult to kill them off; it is difficult to avoid infection of coccidia and prevalence of coccidiosis. At present, control of animal coccidiosis mainly relies on anticoccidial drugs. However, the long-term widespread use of anticoccidial drugs has led to widespread incidence of drug resistance, especially of the chicken coccidia. In China, coccidia have shown a high resistance to almost all the existing drugs in chicken husbandry, and thus there is an urgent need to develop a novel anticoccidial drug.

SUMMARY

The first object of the present invention is to provide novel derivatives of 1H-imidazole-4,5-dicarboxamide having anticoccidial activity.

The derivatives of the present invention have structural formulae as shown in formulae (I) to (VI):

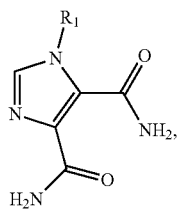

formula (I)

wherein $R_1$ is an aliphatic chain such as n-propyl, isopropyl, n-pentyl or n-hexyl;

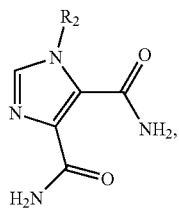

formula (II)

wherein $R_2$ is an aromatic benzyl group such as 2-chloro-6-fluorobenzyl, 4-chlorobenzyl, 3-chlorobenzyl, 2-fluorobenzyl, 4-fluorobenzyl, 4-trifluoromethylbenzyl, 4-methylbenzyl, 4-methoxybenzyl, 2,6-dichlorobenzyl, 3,4-dichlorobenzyl, 4-nitrobenzl, 3,5-dinitrobenzyl, 4-methanesulfonylbenzyl or 4-(4-chlorophenoxy)phenyl;

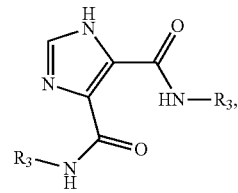

formula (III)

wherein $R_3$ is 4-methylpiperazinyl, 4-nitrophenyl or p-methylphenyl;

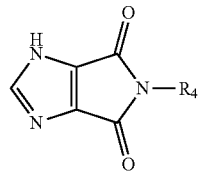

formula (IV)

wherein $R_4$ is H or n-butyl;

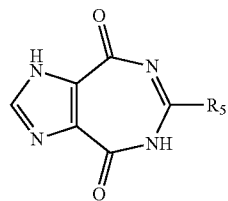

formula (V)

wherein $R_5$ is methyl;

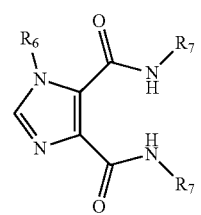

formula (VI)

wherein R₆ is an aromatic benzyl group such as 4-chlorobenzyl or an aliphatic alkyl chain such as ethyl, and R₇ is acetyl or propionyl.

Said coccidia are preferably *Eimeria tenella, Eimeria acervulina, Eimeria maxima* or *Eimeria necatrix*.

Said anticoccidial drug is preferably a drug against poultry coccidia.

Said poultry is preferably chicken.

The second object of the present invention is to provide an anticoccidial drug comprising an effective amount of the derivatives as an active ingredient.

Said coccidia are preferably *Eimeria tenella, Eimeria acervulina, Eimeria maxima* or *Eimeria necatrix*.

Said anticoccidial drug is preferably a drug against poultry coccidia.

Said poultry is preferably chicken.

The derivatives of 1H-imidazole-4,5-dicarboxamide as disclosed in the present invention have significant anticoccidial effect, especially against coccidia that show a resistance to other anticoccidial drugs, and thus they can be used in preparation of anticoccidial drug. The present invention allows the development of novel anticoccidial drugs.

DETAILED DESCRIPTION OF THE EMBODIMENTS

The following embodiments are explanation for the present invention, but not used for limiting the present invention.

Embodiment 1

Preparation of the Derivatives of 1H-imidazole-4,5-dicarboxamide

No. 1:

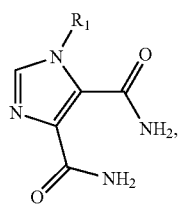

Formula (I)

wherein $R_1$ is an aliphatic chain such as n-propyl, isopropyl, n-pentyl or n-hexyl.

1.1 Preparation of dimethyl 1H-imidazole-4,5-dicarboxylate 100 ml of methanol was added into 1H-imidazole-4,5-dicarboxylic acid (10 g, 64 mmol, 1 eq), and then the mixture was cooled to −9° C. in a low temperature cooler and added with thionyl chloride (5 to 10 eq). The mixture was then heated gradually to a reflux temperature and refluxed with stirring over-night, until it turned from a white turbid solution into a colorless transparent liquid. The solvent was then removed from the mixture by a rotary evaporator with a water pump in a water bath of 40° C. and thereby a white solid was obtained. The solid was washed with a dilute aqueous solution of sodium hydroxide and dried in an oven at 40° C. to obtain a product (dimethyl 1H-imidazole-4,5-dicarboxylate).

¹HNMR (DMSO, 500 MHz): δ 8.057 (1H, s), δ 3.815 (6H, s).

1.2 Preparation of 1-propyl-1H-imidazole-4,5-dicarboxamide (IST15038)

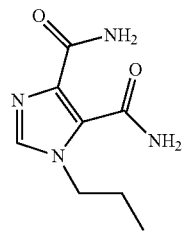

Step 1: Preparation of dimethyl 1-propyl-1H-imidazole-4,5-dicarboxylate

Free dimethyl 1H-imidazole-4,5-dicarboxylate (7.6 g, 41 mmol, 1 eq), 1-bromopropane (1 to 4 eq) and potassium carbonate (0.5 to 4 eq) were dissolved in about 50 ml of DMF, and then the mixture was heated to 50 to 120° C. and stirred for 3 to 24 hours. TLC (PE:EA=1:1) showed that the dimethyl 1H-imidazole-4,5-dicarboxylate was reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-propyl-1H-imidazole-4,5-dicarboxamide

The product obtained in the previous step was added with about 50 ml of ammonia solution, and stirred at 10 to 120° C. for 2 to 24 hours. TLC (PE:EA=1:1) showed that the raw materials were reacted completely. Precipitate was observed in the solution. After filtration, the filter cake was washed with water and then dried at 55° C. to obtain 3.5 g of product (1-propyl-1H-imidazole-4,5-dicarboxamide), with a total yield of 36%.

¹HNMR (CDCl₃, 500 MHz): δ 10.929 (1H, s), δ 7.545 (1H, s), δ 7.458 (1H, s), δ 5.641 (2H, d), δ 4.428-4.457 (2H, m), δ 1.807-1.880 (2H, m), δ 0.912-0.942 (3H, m).

1.3 Preparation of 1-isopropyl-1H-imidazole-4,5-dicarboxamide (IST15115)

Step 1: Preparation of dimethyl 1-propyl-1H-imidazole-4,5-dicarboxylate

Free dimethyl 1H-imidazole-4,5-dicarboxylate (8 g, 43.4 mmol, 1 eq), 2-bromopropane (1 to 4 eq) and potassium carbonate (0.5 to 4 eq) were dissolved in about 80 ml of DMF, and then the mixture was heated to 50 to 120° C. and stirred for 3 to 24 hours. TLC (PE:EA=2:1) showed that the raw materials were reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-isopropyl-1H-imidazole-4,5-dicarboxamide

The product obtained in the previous step was added with about 50 ml of ammonia solution and stirred at 10 to 120° C. for 2 to 24 hours, resulting in a decrease of the thick liquid raw material accompanied by precipitation of white solid. TLC (PE:EA=1:1) showed that the raw materials were reacted completely. After filtration, the filter cake was washed with water and then dried at 55° C. to obtain 3.8 g of product (1-isopropyl-1H-imidazole-4,5-dicarboxamide), with a total yield of 44%.

$^1$H (DMSO, 500 MHz): δ 10.520 (1H, s), δ 8.102 (1H, s), δ 7.912 (1H, s), δ 7.703 (1H, s), δ 7.542 (1H, s), δ 5.607-5.553 (1H, m), δ 1.435-1.422 (6H, m).

1.4 Preparation of 1-pentyl-1H-imidazole-4,5-dicarboxamide (IST15116)

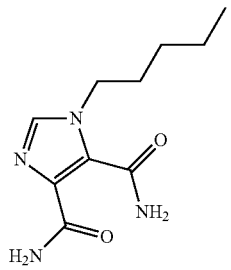 [SMILES: CCCCCn1cnc(C(N)=O)c1C(N)=O]

Step 1: Preparation of dimethyl 1-pentyl-1H-imidazole-4,5-dicarboxylate

Free dimethyl 1H-imidazole-4,5-dicarboxylate (8 g, 43.4 mmol, 1 eq), 1-bromopentane (1 to 4 eq) and potassium carbonate (0.5 to 4 eq) were dissolved in about 80 ml of DMF, and then the mixture was heated to 50 to 120° C. and stirred for 3 to 24 hours. TLC (PE:EA=2:1) showed that the raw materials were reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-pentyl-1H-imidazole-4,5-dicarboxamide

The product obtained in the previous step was added with about 50 ml of ammonia solution and stirred at 10 to 120° C. for 2 to 24 hours, resulting in a decrease of the thick liquid raw material accompanied by precipitation of white solid. TLC (PE:EA=1:1) showed that the raw materials were reacted completely. After filtration, the filter cake was washed with water and then dried at 55° C. to obtain 8.2 g of product (1-pentyl-1H-imidazole-4,5-dicarboxamide), with a total yield of 67%.

$^1$H NMR (DMSO, 500 MHz): δ 10.617 (1H, s), δ 7.927 (1H, s), δ 7.915 (1H, s), δ 7.737 (1H, s), δ 7.505 (1H, s), δ 4.416-4.388 (2H, m), δ 1.709-1.650 (2H, m), 1.301-1.244 (2H, m), δ 1.208-1.162 (2H, m), δ 0.85 (3H, m).

1.5 Preparation of 1-hexyl-1H-imidazole-4,5-dicarboxamide (IST15162)

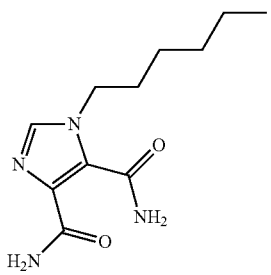 [SMILES: CCCCCCn1cnc(C(N)=O)c1C(N)=O]

Step 1: Preparation of dimethyl 1-hexyl-1H-imidazole-4,5-dicarboxylate

Free dimethyl 1H-imidazole-4,5-dicarboxylate (9.2 g, 50 mmol, 1 eq), 1-bromohexane (1 to 4 eq) and potassium carbonate (0.5 to 4 eq) were dissolved in about 80 ml of DMF, and then the mixture was heated to 50 to 120° C. and stirred for 3 to 24 hours. TLC (PE:EA=2:1) showed that the raw materials were reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-hexyl-1H-imidazole-4,5-dicarboxamide

The product obtained in the previous step was added with about 50 ml of ammonia solution and stirred at 10 to 120° C. for 2 to 24 hours, resulting in a decrease of the thick liquid raw material accompanied by precipitation of white solid. TLC (PE:EA=1:1) showed that the raw materials were reacted completely. After filtration, the filter cake was washed with water and then dried at 55° C. to obtain 8.3 g of product (1-hexyl-1H-imidazole-4,5-dicarboxamide), with a total yield of 69%.

$^1$H NMR (DMSO, 500 MHz): δ 10.615 (1H, s), δ 7.916 (2H, s), δ 7.736 (1H, s), δ 7.505 (1H, s), δ 4.387-4.416 (2H, m), δ 1.642-1.700 (2H, m), δ 1.187-1.278 (6H, m), δ 0.852 (3H, m).

No. 2:

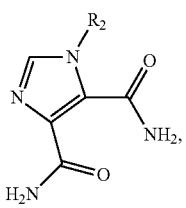

Formula (II)

wherein R₂ is an aromatic benzyl group such as 2-chloro-6-fluorobenzyl, 4-chlorobenzyl, 3-chlorobenzyl, 4-fluorobenzyl, 4-trifluoromethylbenzyl, 4-methoxybenzyl, 3,4-dichlorobenzyl, 3,5-dinitrobenzyl or 4-methanesulfonylbenzyl.

1.6 Preparation of 1-(2-chloro-6-fluorobenzyl)-1H-imidazole-4,5-dicarboxamide (IST15031)

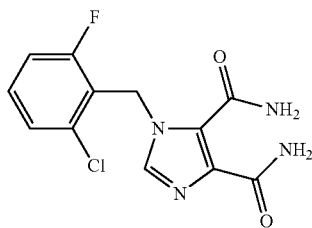 [SMILES: NC(=O)c1ncn(Cc2c(F)cccc2Cl)c1C(N)=O]

Step 1: Preparation of dimethyl 1-(2-chloro-6-fluoro-benzyl)-1H-imidazole-4,5-dicarboxylate Free dimethyl 1H-imidazole-4,5-dicarboxylate (9.2 g, 50 mmol, 1 eq), 2-chloro-6-fluorobenzyl chloride (1 to 5 eq) and potassium carbonate (0.2 to 5 eq) were dissolved in about 70 ml of DMF, and then the mixture was stirred at 30 to 120° C. for 3 to 24 hours. TLC (PE:EA=1:1) showed that the dimethyl 1H-imidazole-4,5-dicarboxylate was reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-(2-chloro-6-fluorobenzyl)-1H-imidazole-4,5-dicarboxamide The product obtained in the previous step was dissolved in about 50 ml of ammonia solution and stirred at 10 to 150° C. for 2 to 24 hours. During the stirring the reactants decreased gradually accompanied by precipitation of a large amount of white solid. After filtration, the filter cake was washed with water and then dried at 55° C. to obtain a product (1-(2-chloro-6-fluorobenzyl)-1H-imidazole-4,5-dicarboxamide).

$^1$H NMR (DMSO, 500 MHz): δ 10.563 (1H, s), δ 7.954 (1H, s), δ 7.794 (1H, s), δ 7.659 (1H, s), δ 7.579 (1H, s), δ 7.424-7.468 (1H, m), δ 7.370-7.386 (1H, d), δ 7.229-7.268 (1H, m), δ 5.826 (2H, s).

1.7 Preparation of 1-(4-chlorobenzyl)-1H-imidazole-4,5-dicarboxamide (IST15037)

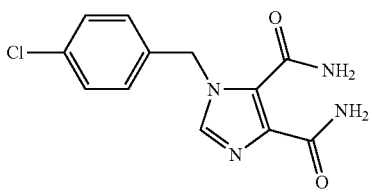 [SMILES: NC(=O)c1ncn(Cc2ccc(Cl)cc2)c1C(N)=O]

Step 1: Preparation of dimethyl 1-(4-chlorobenzyl)-1H-imidazole-4,5-dicarboxylate Free dimethyl 1H-imidazole-4,5-dicarboxylate (7.6 g, 41 mmol, 1 eq), 4-chlorobenzyl chloride (1 to 5 eq) and potassium carbonate (0.2 to 5 eq) were dissolved in about 50 ml of DMF, and then the mixture was stirred at 30 to 120° C. for 3 to 24 hours. TLC (PE:EA=1:1) showed that the dimethyl 1H-imidazole-4,5-dicarboxylate was reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-(4-chlorobenzyl)-1H-imidazole-4,5-dicarboxamide

The product obtained in the previous step was added with about 50 ml of ammonia solution and stirred at 10 to 150° C. for 2 to 24 hours. TLC (PE:EA=1:1) showed that the raw materials were reacted completely, and precipitate was observed. After filtration, the filter cake was washed with water and then dried at 55° C. to obtain 5 g of product (1-(4-chlorobenzyl)-1H-imidazole-4,5-dicarboxamide), with a yield of 44%.

$^1$HNMR (CDCl₃, 500 MHz): δ 10.931 (1H, s), δ 7.6 (1H, s), δ 7.505 (1H, s), δ 7.301-7.318 (2H, d), δ 7.135-7.152 (2H, d), δ 5.708 (2H, s), δ 5.578-5.603 (2H, s).

1.8 Preparation of 1-(3-chlorobenzyl)-1H-imidazole-4,5-dicarboxamide (IST15041)

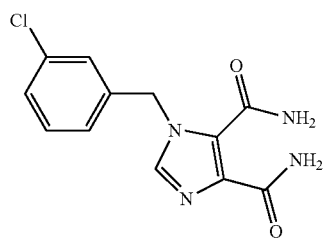 [SMILES: NC(=O)c1ncn(Cc2cccc(Cl)c2)c1C(N)=O]

Step 1: Preparation of dimethyl 1-(3-chlorobenzyl)-1H-imidazole-4,5-dicarboxylate Free dimethyl 1H-imidazole-4,5-dicarboxylate (5 g, 27 mmol, 1 eq), 3-chlorobenzyl bromide (1 to 5 eq) and potassium carbonate (0.2 to 5 eq) were dissolved in about 50 ml of DMF, and then the mixture was stirred at 30 to 120° C. for 3 to 24 hours. TLC (PE:EA=1:1) showed that the dimethyl 1H-imidazole-4,5-dicarboxylate was reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-(3-chlorobenzyl)-1H-imidazole-4,5-dicarboxamide

The product obtained in the previous step was added with about 50 ml of ammonia solution and stirred at 10 to 150° C. for 2 to 24 hours. TLC (PE:EA=1:1) showed that the raw materials were reacted completely, and precipitate was observed. After filtration, the filter cake was washed with water and then dried at 55° C. to obtain 5.3 g of product (1-(3-chlorobenzyl)-1H-imidazole-4,5-dicarboxamide), with a total yield of 71%.

$^1$HNMR (DMSO, 500 MHz): δ 10.641 (1H, s), δ 8.138 (1H, s), δ 8.009 (1H, s), δ 7.821 (1H, s), δ 7.556 (1H, s), δ 7.331-7.369 (2H, m), δ 7.240 (1H, s), δ 7.094-7.108 (1H, d), δ 5.713 (2H, s).

1.9 Preparation of 1-(4-fluorobenzyl)-1H-imidazole-4,5-dicarboxamide (IST15042)

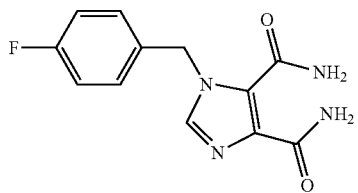 [SMILES: NC(=O)c1ncn(Cc2ccc(F)cc2)c1C(N)=O]

Step 1: Preparation of dimethyl 1-(4-fluorobenzyl)-1H-imidazole-4,5-dicarboxylate Free dimethyl 1H-imidazole-4,5-dicarboxylate (8.37 g, 45.5 mmol, 1 eq), 4-fluorobenzyl chloride (1 to 5 eq) and potassium carbonate (0.2 to 5 eq) were dissolved in about 70 ml of DMF, and then the mixture was stirred at 30 to 120° C. for 3 to 24 hours. TLC (PE:EA=1:1) showed that the dimethyl 1H-imidazole-4,5-dicarboxylate was reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-(4-fluorobenzyl)-1H-imidazole-4,5-dicarboxamide

The product obtained in the previous step was added with about 50 ml of ammonia solution and stirred at 10 to 150° C. for 2 to 24 hours. TLC (PE:EA=1:1) showed that the raw materials were reacted completely, and precipitate was observed. After filtration, the filter cake was washed with water and then dried at 55° C. to obtain 2.9 g of product (1-(4-fluorobenzyl)-1H-imidazole-4,5-dicarboxamide), with a total yield of 24.4%.

$^1$HNMR (DMSO, 500 MHz): δ 10.622 (1H, s), δ 8.110 (1H, s), ι 7.985 (1H, s), δ 7.795 (1H, s), δ 7.534 (1H, s), δ 7.229-7.258 (2H, m), δ 7.127-7.162 (2H, m), δ 5.696 (2H, s).

1.10 Preparation of 1-(2-fluorobenzyl)-1H-imidazole-4,5-dicarboxamide (IST15043)

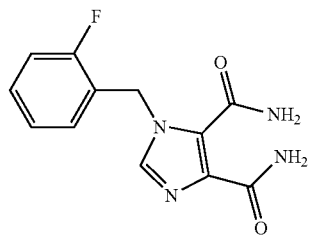 [SMILES: NC(=O)c1ncn(Cc2ccccc2F)c1C(N)=O]

Step 1: Preparation of dimethyl 1-(2-fluorobenzyl)-1H-imidazole-4,5-dicarboxylate Free dimethyl 1H-imidazole-4,5-dicarboxylate (11.2 g, 60.9 mmol, 1 eq), 2-fluorobenzyl chloride (1 to 5 eq) and potassium carbonate (0.2 to 5 eq) were dissolved in about 80 ml of DMF, and then the mixture was stirred at 30 to 120° C. for 3 to 24 hours. TLC (PE:EA=1:1) showed that the dimethyl 1H-imidazole-4,5-dicarboxylate was reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-(2-fluorobenzyl)-1H-imidazole-4,5-dicarboxamide

The product obtained in the previous step was added with about 100 ml of ammonia solution and stirred at 10 to 150° C. for 2 to 24 hours. TLC (PE:EA=1:1) showed that the raw materials were reacted completely, and precipitate was observed. After filtration, the filter cake was washed with water and then dried at 55° C. to obtain 11 g of product (1-(2-fluorobenzyl)-1H-imidazole-4,5-dicarboxamide), with a total yield of 68.8%.

$^1$H (DMSO, 500 MHz): δ 10.641 (1H, s), δ 8.05 (1H, s), δ 8.04 (1H, s), δ 7.824 (1H, s), δ 7.511 (1H, s), δ 7.303-7.348 (1H, m), δ 7.179-7.218 (1H, m), δ 7.110-7.142 (1H, m), δ 6.820-6.854 (1H, d), δ 5.778 (2H, s).

1.11 Preparation of 1-(2,6-dichlorobenzyl)-1H-imidazole-4,5-dicarboxamide (IST15044)

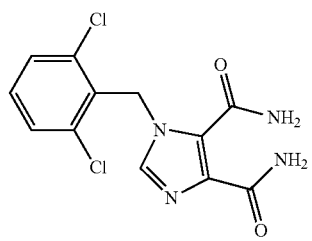 [SMILES: NC(=O)c1ncn(Cc2c(Cl)cccc2Cl)c1C(N)=O]

Step 1: Preparation of dimethyl 1-(2,6-dichlorobenzyl)-1H-imidazole-4,5-dicarboxylate Free dimethyl 1H-imidazole-4,5-dicarboxylate (8.37 g, 45.5 mmol, 1 eq), 2,6-dichlorobenzyl chloride (1 to 5 eq) and potassium carbonate (0.2 to 5 eq) were dissolved in about 50 ml of DMF, and then the mixture was stirred at 30 to 120° C. for 3 to 24 hours. TLC (PE:EA=1:1) showed that the dimethyl 1H-imidazole-4,5-dicarboxylate was reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-(2,6-dichlorobenzyl)-1H-imidazole-4,5-dicarboxamide The product obtained in the previous step was added with about 50 ml of ammonia solution and stirred at 10 to 150° C. for 2 to 24 hours. TLC (PE:EA=1:1) showed that the raw materials were reacted completely, and precipitate was observed. After filtration, the filter cake was washed with water and then dried at 55° C. to obtain 7.5 g of product (1-(2,6-dichlorobenzyl)-1H-imidazole-4,5-dicarboxamide), with a total yield of 54%.

$^1$HNMR (DMSO, 500 MHz): δ 10.646 (1H, s), δ 7.942 (1H, s), δ 7.809 (1H, s), δ 7.684 (1H, s), δ 7.583-7.600 (2H, d), δ 7.479-7.511 (1H, m), δ 7.276 (1H, s), δ 5.876 (2H, s).

1.12 Preparation of 1-(4-nitrobenzyl)-1H-imidazole-4,5-dicarboxamide (IST15045)

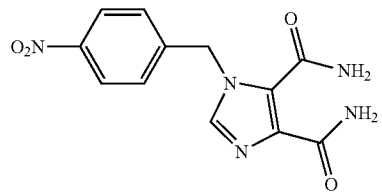 [SMILES: NC(=O)c1ncn(Cc2ccc([N+](=O)[O-])cc2)c1C(N)=O]

Step 1: Preparation of dimethyl 1-(4-nitrobenzyl)-1H-imidazole-4,5-dicarboxylate Free dimethyl 1H-imidazole-4,5-dicarboxylate (6 g, 32.6 mmol, 1 eq), 4-nitrobenzyl chloride (1 to 5 eq) and potassium carbonate (0.2 to 5 eq) were dissolved in about 50 ml of DMF, and then the mixture was stirred at 30 to 120° C. for 3 to 24 hours. TLC (PE:EA=1:1) showed that the dimethyl 1H-imidazole-4,5-dicarboxylate was reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-(4-nitrobenzyl)-1H-imidazole-4,5-dicarboxamide

The product obtained in the previous step was dissolved in about 50 ml of ammonia solution and stirred at 10 to 150° C. for 2 to 24 hours. During the stirring the reactants decreased gradually accompanied by precipitation of a large amount of white solid. After filtration, the filter cake was washed with water and then dried at 55° C. to obtain a product (1-(4-nitrobenzyl)-1H-imidazole-4,5-dicarboxamide), with a total yield of 50.5%.

$^1$H (DMSO, 500 MHz): δ 10.664 (1H, s), δ 8.161-8.195 (3H, m), δ 8.041 (1H, s), δ 7.847 (1H, s), δ 7.526 (1H, s), δ 7.329-7.347 (2H, d), δ 5.839 (2H, s).

1.13 Preparation of 1-(4-methylbenzyl)-1H-imidazole-4,5-dicarboxamide (IST15046)

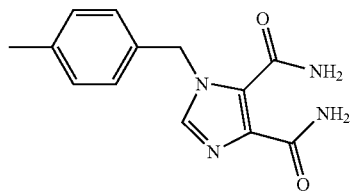 [SMILES: Cc1ccc(Cn2cnc(C(N)=O)c2C(N)=O)cc1]

Step 1: Preparation of dimethyl 1-(4-methylbenzyl)-1H-imidazole-4,5-dicarboxylate Free dimethyl 1H-imidazole-4,5-dicarboxylate (7 g, 38 mmol, 1 eq), 4-methylbenzyl chloride (1 to 5 eq) and potassium carbonate (0.2 to 5 eq) were dissolved in about 50 ml of DMF, and then the mixture was stirred at 30 to 120° C. for 3 to 24 hours. TLC (PE:EA=1:2) showed that the dimethyl 1H-imidazole-4,5-dicarboxylate was reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-(4-methylbenzyl)-1H-imidazole-4,5-dicarboxamide

The product obtained in the previous step was added with about 50 ml of ammonia solution and stirred at 10 to 150° C. for 2 to 24 hours. During the stirring the thick liquid raw materials decreased gradually accompanied by precipitation of white solid. TLC (PE:EA=1:2) showed that the raw materials were reacted completely. After filtration, the filter cake was washed with water and then dried at 55° C. to obtain 7.8 g of product (1-(4-methylbenzyl)-1H-imidazole-4,5-dicarboxamide), with a total yield of 79%.

$^1$HNMR (DMSO, 500 MHz): δ 10.583 (1H, s), δ 8.069 (1H, s), δ 7.968 (1H, s), δ 7.776 (1H, s), δ 7.503 (1H, s), δ 7.126-7.110 (2H, d), δ 7.074-7.058 (2H, d), δ 5.671 (2H, s), δ 2.254 (3H, s).

1.14 Preparation of 1-(4-(trifluromethyl)benzyl)-1H-imidazole-4,5-dicarboxamide (IST15051)

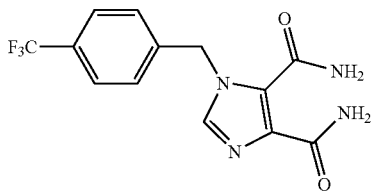 [SMILES: NC(=O)c1ncn(Cc2ccc(C(F)(F)F)cc2)c1C(N)=O]

Step 1: Preparation of dimethyl 1-(4-(triflurom-ethyl)benzyl)-1H-imidazole-4,5-dicarboxylate Free dimethyl 1H-imidazole-4,5-dicarboxylate (7 g, 38 mmol, 1 eq), 4-(trifluromethyl)benzyl bromide (1 to 5 eq) and potassium carbonate (0.2 to 5 eq) were dissolved in about 60 ml of DMF, and then the mixture was stirred at 30 to 120° C. for 3 to 24 hours. TLC (PE:EA=1:2) showed that the dimethyl 1H-imidazole-4,5-dicarboxylate was reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-(4-(triflluromethyl)benzyl)-1H-imidazole-4,5-dicarboxamide The product obtained in the previous step was added with about 50 ml of ammonia solution and stirred at 10 to 150° C. for 2 to 24 hours. During the stirring the thick liquid raw materials decreased gradually accompanied by precipitation of white solid. TLC (PE:EA=1:2) showed that the raw materials were reacted completely. After filtration, the filter cake was washed with water and then dried at 55° C. to obtain 8.73 g of product (1-(4-(trifluromethyl)benzyl)-1H-imidazole-4,5-dicarboxamide), with a total yield of 73%.

$^1$HNMR (DMSO, 500 MHz): δ 10.651 (1H, s), δ 8.149 (1H, s), δ 8.026 (1H, s), δ 7.833 (1H, s), δ 7.697-7.681 (2H, d), δ 7.524 (1H, s), δ 7.319-7.303 (2H, d), δ 5.808 (2H, s).

1.15 Preparation of 1-(4-methoxybenzyl)-1H-imidazole-4,5-dicarboxamide (IST15053)

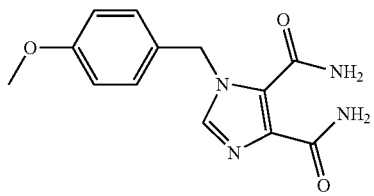 [SMILES: COc1ccc(Cn2cnc(C(N)=O)c2C(N)=O)cc1]

Step 1: Preparation of dimethyl 1-(4-methoxybenzyl)-1H-imidazole-4,5-dicarboxylate Free dimethyl 1H-imidazole-4,5-dicarboxylate (9.2 g, 50 mmol, 1 eq), 4-methoxybenzyl chloride (1 to 5 eq) and potassium carbonate (0.2 to 5 eq) were dissolved in about 70 ml of DMF, and then the mixture was stirred at 30 to 120° C. for 3 to 24 hours. TLC (PE:EA=1:2) showed that the dimethyl 1H-imidazole-4,5-dicarboxylate was reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-(4-methoxybenzyl)-1H-imidazole-4,5-dicarboxamide

The product obtained in the previous step was added with about 80 ml of ammonia solution and stirred at 10 to 150° C. for 2 to 24 hours. During the stirring the light-yellow thick liquid raw materials decreased gradually accompanied by precipitation of white solid. TLC (PE:EA=1:2) showed that the raw materials were reacted completely. After filtration, the filter cake was washed with water and then dried at 50° C. to obtain 8.55 g of product (1-(4-methoxybenzyl)-1H-imidazole-4,5-dicarboxamide), with a total yield of 62%.

$^1$HNMR (DMSO, 500 MHz): δ 10.587 (1H, s), δ 8.069 (1H, s), δ 7.957 (1H, s), δ 7.766 (1H, s), δ 7.519 (1H, s), δ 7.180-7.163 (2H, d), δ 6.881-6.864 (2H, d), δ 5.640 (2H, s).

1.16 Preparation of 1-(3,4-dichlorobenzyl)-1H-imidazole-4,5-dicarboxamide (IST15054)

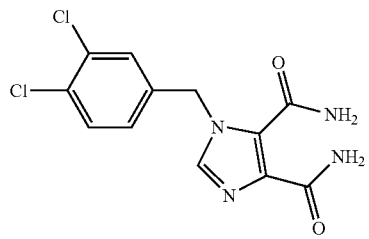 [SMILES: NC(=O)c1ncn(Cc2ccc(Cl)c(Cl)c2)c1C(N)=O]

Step 1: Preparation of dimethyl 1-(3,4-dichloroben-zyl)-1H-imidazole-4,5-dicarboxylate Free dimethyl 1H-imidazole-4,5-dicarboxylate (9.2 g, 50 mmol, 1 eq), 3,4-dichlorobenzyl bromide (1 to 5 eq) and potassium carbonate (0.2 to 5 eq) were dissolved in about 70 ml of DMF, and then the mixture was stirred at 30 to 120° C. for 3 to 24 hours. TLC (PE:EA=1:2) showed that the dimethyl 1H-imidazole-4,5-dicarboxylate was reacted almost completely, and a new spot appeared. The mixture was added with 150 ml of water and further added with 200 ml of ethyl acetate, and thereby the layers were separated. The organic layer was washed with 200 ml of water and dried by a rotary evaporator to obtain a transparent liquid which was used in the next step.

Step 2: Preparation of 1-(3,4-dichlorobenzyl)-1H-imidazole-4,5-dicarboxamide The product obtained in the previous step was added with about 80 ml of ammonia solution and stirred at 10 to 150° C. for 2 to 24 hours. During the stirring the light-yellow thick liquid raw materials decreased gradually accompanied by precipitation of white solid. TLC (PE:EA=1:2) showed that the raw materials were reacted completely. After filtration, the filter cake was washed with water and then dried at 50° C. to obtain 11.8 g of product (1-(3,4-dichlorobenzyl)-1H-imidazole-4,5-dicarboxamide), with a total yield of 75%.

1HNMR (DMSO, 500 MHz): δ 10.653 (1H, s), δ 8.146 (1H, s), δ 8.014 (1H, s), δ 7.827 (1H, s), δ 7.595-7.569 (2H, m), δ 7.473 (1H, s), δ 7.131-7.111 (1H, d), δ 5.689 (2H, s).

1.17 Preparation of 1-(3,5-dinitrobenzyl)-1H-imidazole-4,5-dicarboxamide (IST15056)

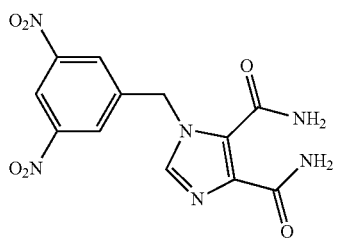 [SMILES: NC(=O)c1ncn(Cc2cc([N+](=O)[O-])cc([N+](=O)[O-])c2)c1C(N)=O]

Step 1: Preparation of (3,5-dinitrophenyl)methanol 3,5-Dinitrobenzoic acid (12 g, 56.6 mmol, 1 eq) was dissolved in about 100 ml of tetrahydrofuran. The mixture was cooled to 0° C. and then added with sodium borohydride (0.5 to 5 eq). After stirred for 0.1 to 1 hour, the mixture was slowly added with boron trifluoride etherate (0.1 to 6 eq), heated to room temperature, stirred under room temperature until it was difficult to stir, and then slowly poured into cold dilute aqueous solution of hydrochloric acid and added with ethyl acetate such that the layers were separated. The organic layer was separated by silica gel column chromatography to obtain a product.

$^1$HNMR (DMSO, 500 MHz): δ 8.718 (1H, s), δ 8.579 (2H, s), δ 5.796 (1H, m), δ 4.763 (2H, d).

Step 2: Preparation of 1-(chloromethyl)-3,5-dinitrobenzene (3,5-Dinitrophenyl)methanol (2.4 g, 12.12 mmol, 1 eq) was dissolved in dichloromethane. The mixture was cooled to 0° C., added with triethylamine (2 to 8 eq), and then slowly added with thionyl chloride (1 to 6 eq) dropwise. During the addition of thionyl chloride white smoke was observed. The mixture was then heated to a reflux temperature, and refluxed for 2 to 3 hours. TLC showed a new spot. The mixture was then separated by silica gel column chromatography to obtain a product.

Step 3: Preparation of dimethyl 1-(3,5-dinitrobenzyl)-1H-imidazole-4,5-dicarboxylate Dimethyl 1H-imidazole-4,5-dicarboxylate (1.28 g, 6.94 mmol, 1 eq), 1-(chloromethyl)-3,5-dinitrobenzene (1 to 5 eq) and potassium carbonate (0.2 to 5 eq) were dissolved in about 5 ml of DMF, and then the mixture was stirred at 30 to 120° C. for 3 to 24 hours. TLC showed that the dimethyl 1H-imidazole-4,5-dicarboxylate was reacted almost completely, and showed a new spot with low polarity while an dark impurity spot appeared at the initial spot. Ethyl acetate and water were added and then the layers were separated. The organic layer was then separated by silica gel column chromatography to obtain a product which was used in the next step.

Step 4: Preparation of 1-(3,5-dinitrobenzyl)-1H-imidazole-4,5-dicarboxamide

The product obtained in the previous step was added with about 50 ml of ammonia solution and stirred at 10 to 150° C. for 2 to 24 hours. A large amount of grey solid was precipitated. TLC showed that the raw material and the product were generally identical in polarity. After filtration, the filter cake was dried at 40° C. in an oven to obtain the product (1-(3,5-dinitrobenzyl)-1H-imidazole-4,5-dicarboxamide).

$^1$H (DMSO, 500 MHz): δ 10.727 (1H, s), δ 8.748 (1H, s), δ 8.517 (2H, s), δ 8.287 (1H, s), δ 8.062 (1H, s), δ 7.871 (1H, s), δ 7.665 (1H, s), δ 5.908 (2H, s).

1.18 Preparation of 1-(4-(methylsulfonyl)benzyl)-1H-imidazole-4,5-dicarboxamide (IST15150)

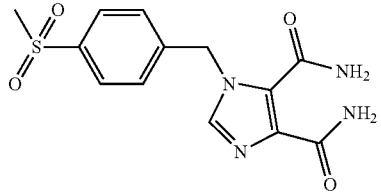 [SMILES: CS(=O)(=O)c1ccc(Cn2cnc(C(N)=O)c2C(N)=O)cc1]

Step 1: Preparation of (4-(methylsulfonyl)phenyl)methanol

4-Methylsulfonylbenzoic acid (12 g, 60.3 mmol, 1 eq) was dissolved in about 100 ml of tetrahydrofuran. The mixture was cooled to 0° C. and then added with sodium borohydride (0.5 to 5 eq). And then the mixture was slowly added with boron trifluoride etherate (0.1 to 6 eq), heated to room temperature, stirred under room temperature over night. TLC showed a new spot with relatively low polarity. The mixture was then slowly poured into cold water and added with ethyl acetate such that the layers were separated. The organic layer was dried by a rotary evaporator to obtain a product.

$^1$H (DMSO, 500 MHz): δ 7.888-7.905 (2H, d), δ 7.543-7.560 (2H, d), δ 4.806 (2H, s), δ 3.035 (3H, s).

Step 2: Preparation of 1-(chloromethyl)-4-(methyl sulfonyl)benzene (4-(Methylsulfonyl)phenyl)methanol (11.16 g, 60 mmol, 1 eq) was dissolved in dichloromethane. The mixture was cooled to 0° C., added with triethylamine (2 to 8 eq), and then slowly added with thionyl chloride (1 to 6 eq) dropwise. During the addition of thionyl chloride white smoke was observed. The mixture was then heated to a reflux temperature, and refluxed for 2 to 3 hours. TLC showed a new spot with relative low polarity and the raw materials were reacted completely. The solution was then poured into cold water and then the layers were separated. The organic layer was dried by a rotary evaporator and the residual was used in the next step.

Step 3: Preparation of dimethyl 1-(4-(methylsulfonyl)benzyl)-1H-imidazole-4,5-dicarboxylate Dimethyl 1H-imidazole-4,5-dicarboxylate (9.2 g, 50 mmol, 1 eq), 1-(chloromethyl)-4-(methylsulfonyl)benzene (1 to 5 eq) and potassium carbonate (0.2 to 5 eq) were dissolved in about 50 ml of DMF, and then the mixture was stirred at 30 to 120° C. for 3 to 24 hours. TLC showed that the 1-(chloromethyl)-4-(methylsulfonyl)benzene was reacted almost completely. The mixture was cooled to room temperature and then added with water and ethyl acetate and thereby the layers were separated. The solvent was removed from the organic layer by a rotary evaporator to obtain a product which was used in the next step.

Step 4: Preparation of 1-(4-(methylsulfonyl)benzyl)-1H-imidazole-4,5-dicarboxamide The product obtained in the previous step was added with about 50 ml of ammonia solution and stirred at 10 to 150° C. for 2 to 24 hours. A large amount of grey solid was precipitated. After filtration, the filter cake was dried at 50° C. to obtain 8 g of product (1-(4-(methylsulfonyl)benzyl)-1H-imidazole-4,5-dicarboxamide), with a total yield of 41%.

$^1$H (DMSO, 500 MHz): δ 10.666 (1H, s), δ 8.156 (1H, s), δ 8.032 (1H, s), δ 7.868-7.885 (2H, d), δ 7.838 (1H, s), δ 7.527 (1H, s), δ 7.337-7.354 (2H, d), δ 5.823 (2H, s), δ 3.178 (3H, s).

1.19 Preparation of 1-(4-(4-chlorophenoxy)benzyl)-1H-imidazole-4,5-dicarboxamide (IST15167)

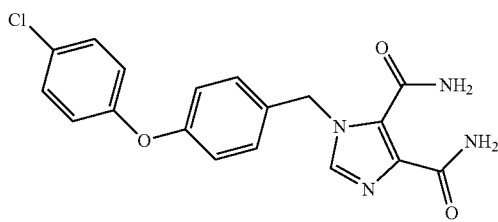 [SMILES: NC(=O)c1ncn(Cc2ccc(Oc3ccc(Cl)cc3)cc2)c1C(N)=O]

Step 1: Preparation of 4-(4-chlorophenoxy)benzaldehyde

4-Fluorobenzaldehyde (18.6 g, 150 mmol, 1 eq), 4-chlorophenol (0.8 to 2 eq) and potassium carbonate (0.2 to 5 eq) were dissolved in 100 ml of DMF. The mixture was stirred at 50 to 120° C. for 3 to 24 hours. TLC showed that the raw materials and the product were generally identical in polarity. The mixture was then cooled to room temperature and added with water and ethyl acetate, and thereby the layers were separated. The organic layer was washed with dilute aqueous solution of sodium hydroxide and then separated by silica gel column chromatography to obtain a product giving a spot close to that of 4-fluorobenzaldehyde on TLC. The product was then used in the next step.

$^1$HNMR (CDCl$_3$, 500 MHz): δ 9.926 (1H, s), δ 7.864-7.847 (2H, d), δ 7.358-7.376 (2H, d), δ 7.013-7.065 (4H, m).

Step 2: Preparation of (4-(4-chlorophenoxy)phenyl)methanol 4-(4-chlorophenoxy)benzaldehyde (11.6 g, 50 mmol, 1 eq) was dissolved in 100 ml of THF. The mixture was cooled to 0° C. and added with lithium aluminum hydride (0.5 to 3 eq) batch by batch. Then the mixture was heated gradually to room temperature and stirred for 3 to 4 hours. TLC showed that 4-(4-chlorophenoxy)benzaldehyde was reacted completely, and showed a spot with relatively high polarity. The mixture was then added with 10H$_2$O.H$_2$SO$_4$ to stop the reaction, and then added with an appropriate amount of ethyl acetate and stirred for half an hour. After filtration, the filter cake was washed with ethyl acetate, and then the organic layer was dried by a rotary evaporator to obtain a product which was used in the next step.

Step 3: Preparation of 1-chloro-4-(4-(chloromethyl)phenoxy)benzene (4-(4-Chlorophenoxy)phenyl)methanol (12 g, 51.3 mmol, 1 eq) was dissolved in 100 ml of dichloromethane. The mixture was cooled to 0° C., added with triethylamine (2 to 8 eq), and then slowly added with thionyl chloride (1 to 6 eq) dropwise. Then the mixture was heated to room temperature and stirred at room temperature for 2 to 3 hours. TLC showed that (4-(4-chlorophenoxy)phenyl)methanol was reacted completely and a new spot appeared. The solution was then added with water and thereby the layers were separated. The organic layer was dried by a rotary evaporator to obtain a crude product which was used in the next step.

Step 4: Preparation of dimethyl 1-(4-(4-chlorophenoxy)benzyl)-1H-imidazole-4,5-dicarboxylate Dimethyl 1H-imidazole-4,5-dicarboxylate (9.2 g, 50 mmol, 1 eq) was dissolved in 60 ml of DMF. The mixture was then added with 1-chloro-4-(4-(chloromethyl)phenoxy)benzene (1 to 5 eq) and potassium carbonate (0.2 to 5 eq), stirred at 30 to 120° C. for 3 to 24 hours. TLC showed that the dimethyl 1H-imidazole-4,5-dicarboxylate was reacted completely and a new spot appeared. The solution was added with 100 ml of water and 100 ml of ethyl acetate and thereby the layers were separated. The organic layer was then separated by silica gel column chromatography to obtain a product.

$^1$HNMR (CDCl$_3$, 500 MHz): δ 7.734 (1H, s), δ 7.287-7.305 (2H, d), δ 7.161-7.178 (2H, d), δ 6.920-6.912 (4H, m), δ 5.389 (2H, s), δ 3.920 (3H, s), δ 3.873 (3H, s).

Step 5: Preparation of 1-(4-(4-chlorophenoxy)benzyl)-1H-imidazole-4,5-dicarboxamide Dimethyl 1-(4-(4-chlorophenoxy)benzyl)-1H-imidazole-4,5-dicarboxylate (10 g, 25 mmol, 1 eq) was added into about 60 ml of ammonia solution and stirred at 10 to 150° C. for 2 to 24 hours. White solid was precipitated. After filtration, the filter cake was dried at 50° C. to obtain a product (1-(4-(4-chlorophenoxy)benzyl)-1H-imidazole-4,5-dicarboxamide).

$^1$HNMR (DMSO, 500 MHz): δ 10.663 (1H, s), δ 8.130 (1H, s), δ 8.026 (1H, s), δ 7.834 (1H, s), δ 7.831 (1H, s), δ 7.400-7.589 (2H, d), δ 7.229-7.252 (2H, d), δ 6.982-7.016 (4H, m), δ 5.707 (2H, s).

No. 3:

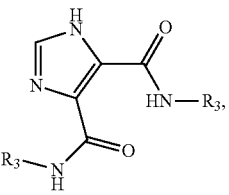

Formula (III)

wherein $R_3$ is 4-methylpiperazinyl, 4-nitrophenyl or p-methylphenyl.

1.20 Preparation of (1H-imidazole-4,5-diyl) bis((4-methylpiperazin-1-yl)methanone) (IST15008)

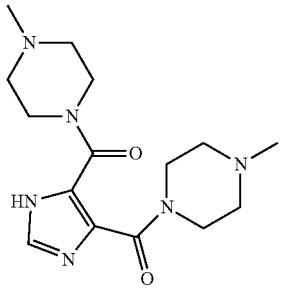 [SMILES: CN1CCN(C(=O)c2nc[nH]c2C(=O)N2CCN(C)CC2)CC1]

Dimethyl 1H-imidazole-4,5-dicarboxylate (9.2 g, 50 mmol, 1 eq) was added with about 50 ml of ethanol and N-methylpiperazine (2 to 6 eq). The mixture was stirred at 10 to 120° C. for 2 to 24 hours, and precipitate was observed. After filtration, the filter cake was washed with 100 ml of ethyl acetate and then washed with 50 ml of ethanol, and dried at 50° C. in an oven to obtain a product ((1H-imidazole-4,5-diyl) bis((4-methylpiperazin-1-yl)methanone)).

$^1$HNMR (DMSO, 500 MHz): δ 7.584 (1H, s), δ 3.026~3.046 (8H, m), δ 2.475-2.485 (8H, m), δ 2.211 (6H, s)

1.21 Preparation of $N^4,N^5$-bis(4-nitrophenyl)-1H-imidazole-4,5-dicarboxamide (IST15009)

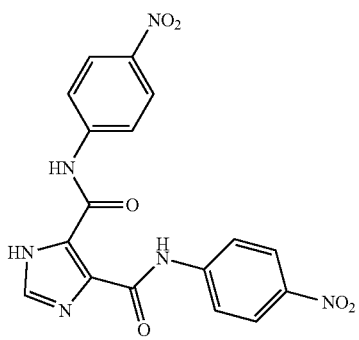 [SMILES: O=C(Nc1ccc([N+](=O)[O-])cc1)c1nc[nH]c1C(=O)Nc1ccc([N+](=O)[O-])cc1]

Dimethyl 1H-imidazole-4,5-dicarboxylate (6 g, 32.6 mmol, 1 eq) was added with about 40 ml of ethanol and 4-Nitroaniline (2 to 6 eq). The mixture was stirred at 10 to 120° C. for 2 to 24 hours, and precipitate was observed. After filtration, the filter cake was washed with 100 ml of ethyl acetate and then washed with 50 ml of ethanol, and dried at 50° C. in an oven to obtain a product ($N^4,N^5$-bis (4-nitrophenyl)-1H-imidazole-4,5-dicarboxamide).

$^1$HNMR (DMSO, 500 MHz): δ 9.057 (1H, s), δ 7.928-7.947 (4H, d), δ 6.588-6.606 (4H, d)

No. 4:

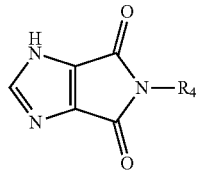

Formula (IV)

wherein $R_4$ is H or n-butyl.

1.22 Preparation of 5-butylpyrrolo[3,4-d]imidazole-4,6(1H,5H)-dione (IST15013)

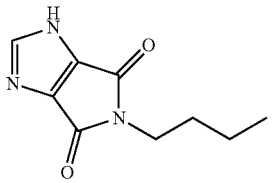

Dimethyl 1H-imidazole-4,5-dicarboxylate (7.8 g, 50 mmol, 1 eq) was added with about 40 ml of ethanol and n-butylamine (1 to 6 eq). The mixture was stirred at 10 to 120° C. for 2 to 24 hours, and precipitate was observed. After filtration, the filter cake was washed with 100 ml of ethyl acetate and then washed with 50 ml of ethanol, and dried at 50° C. in an oven to obtain a product (5-butylpyrrolo [3,4-d]imidazole-4,6(1H,5H)-dione).

$^1$HNMR (DMSO, 500 MHz): δ 7.599 (1H, s), δ 2.793-2.823 (2H, m), δ 1.502-1.517 (2H, dm), δ 1.328-1.343 (2H, m), δ 0.859-0.888 (3H, m)

1.23 Preparation of pyrrolo[3,4-d]imidazole-4,6(1H,5H)-dione (IST15015)

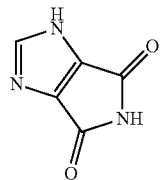

Dimethyl 1H-imidazole-4,5-dicarboxylate (12 g, 77 mmol, 1 eq) was added with about 50 ml of ammonia solution. The mixture was stirred at 10 to 120° C. for 2 to 24 hours, and precipitate was observed. After filtration, the filter cake was washed with 100 ml of water and dried at 50° C. in an oven to obtain a product (pyrrolo[3,4-d]imidazole-4,6(1H,5H)-dione).

$^1$HNMR (DMSO, 500 MHz): δ 7.599 (1H, s)

No. 5:

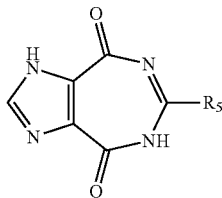

Formula (V)

wherein $R_5$ is methyl.

1.24 Preparation of 6-methylimidazo[4,5-e][1,3]diazepine-4,8(1H,5H)-dione (IST15016)

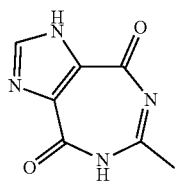

Dimethyl 1H-imidazole-4,5-dicarboxylate (3.68 g, 20 mmol, 1 eq) was added with about 50 ml of ethanol and acetamidine hydrochloride (1 to 6 eq). The mixture was stirred at 10 to 120° C. for 2 to 24 hours, and precipitate was observed. After filtration, the filter cake was washed with 100 ml of water and dried at 50° C. in an oven to obtain 3 g of product (6-methylimidazo[4,5-e][1,3]diazepine-4,8(1H, 5H)-dione), with a yield of 84%.

$^1$HNMR (DMSO, 500 MHz): δ 8.961 (1H, s), δ 8.585 (1H, s), δ 7.625 (1H, s), δ 2.119 (2H, s)

No. 6:

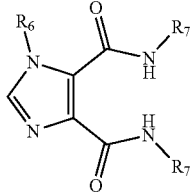

Formula (VI)

wherein $R_6$ is an aromatic benzyl group such as 4-chlorobenzyl or an aliphatic alkyl chain such as ethyl, and $R_7$ is acetyl or propionyl.

1.25 Preparation of $N^4,N^5$-diacetyl-1-(4-chlorobenzyl)-1H-imidazole-4,5-dicarboxamide (IST15151)

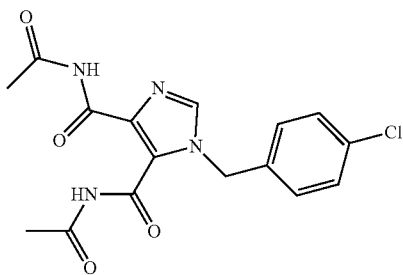 [SMILES: CC(=O)NC(=O)c1ncn(Cc2ccc(Cl)cc2)c1C(=O)NC(C)=O]

Step 1: Preparation of 1H-imidazole-4,5-dicarboxamide

Dimethyl 1H-imidazole-4,5-dicarboxylate (8 g, 43 mmol) was added with about 50 to 100 ml of ammonia solution. The mixture was stirred at 10 to 120° C. for 2 to 24 hours. A large amount of white solid was precipitated. After filtration, the filter cake was washed with 50 ml of water and then washed with 50 ml of ethanol, and dried at 40° C. in an oven to obtain a product.

$^1$HNMR (DMSO, 500 MHz): δ 10.437 (1H, s), δ 9.043 (2H, s), δ 7.769 (1H, s), δ 7.681 (2H, s)

Step 2

1-(4-chlorobenzyl)-1H-imidazole-4,5-dicarboxamide (5 g, 17.9 mmol, 1 eq) and potassium carbonate (1 to 6 eq) were dissolved in 30 ml of acetic anhydride. The mixture was heated to 80 to 150° C. so that the raw materials were dissolved completely, stirred for 2 to 18 hours at the same temperature, then cooled to room temperature and let stand to precipitate a grey solid. After filtration, the filter cake was washed with water and then dried at 50° C. to obtain 3.3 g of product ($N^4,N^5$-diacetyl-1-(4-chlorobenzyl)-1H-imidazole-4,5-dicarboxamide).

$^1$HNMR (DMSO, 500 MHz): δ 11.9546 (1H, s), δ 10.249 (1H, s), δ 8.271 (1H, s), δ 7.404-7.421 (2H, d), δ 7.206-7.223 (2H, d), δ 5.516 (2H, s), δ 2.361 (3H, s), δ 2.227 (3H, s)

1.26 Preparation of 1-(4-chlorobenzyl)-$N^4,N^5$-dipropionyl-1H-imidazole-4,5-dicarboxamide (IST15152)

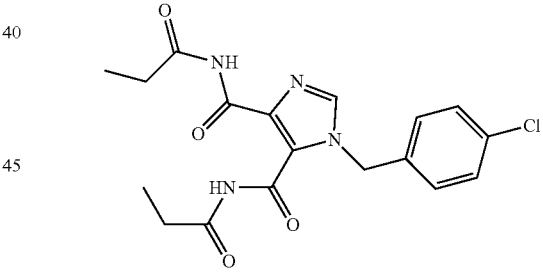

1-(4-chlorobenzyl)-1H-imidazole-4,5-dicarboxamide (5 g, 17.9 mmol, 1 eq) and potassium carbonate (1 to 6 eq) were dissolved in 30 ml of propionic anhydride. The mixture was heated to 80 to 150° C. so that the raw materials were dissolved completely, stirred for 2 to 18 hours at the same temperature, then cooled to room temperature and let stand to precipitate a grey solid. After filtration, the filter cake was washed with water and then dried at 50° C. to obtain 4 g of product (1-(4-chlorobenzyl)-$N^4,N^5$-dipropionyl-1H-imidazole-4,5-dicarboxamide).

$^1$H (CDCl$_3$, 500 MHz): δ 12.951 (1H, s), δ 10.062 (1H, s), δ 7.628 (1H, s), δ 7.314-7.331 (2H, d), δ 7.143-7.160 (2H, d), δ 5.674 (2H, s), δ 2.937-2.980 (2H, m), δ 2.658-2.703 (2H, m), δ 1.198-1.223 (6H, m)

1.27 Preparation of $N^4,N^5$-diacetyl-1-ethyl-1H-imidazole-4,5-dicarboxamide (IST15165)

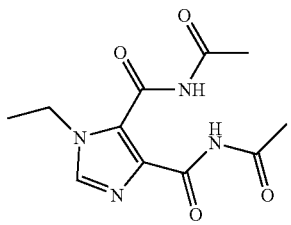 [SMILES: CCn1cnc(C(=O)NC(C)=O)c1C(=O)NC(C)=O]

1-Ethyl-1H-imidazole-4,5-dicarboxamide (11 g, 60.43 mmol, 1 eq) and potassium carbonate (1 to 6 eq) were dissolved in 30 ml of acetic anhydride. The mixture was heated to 80 to 150° C. so that the raw materials were dissolved completely, stirred for 2 to 18 hours at the same temperature, then cooled to room temperature and let stand to precipitate a grey solid. After filtration, the filter cake was washed with water and then dried at 50° C. to obtain 4 g of product ($N^4,N^5$-diacetyl-1-ethyl-1H-imidazole-4,5-dicarboxamide).

$^1$HNMR (DMSO, 500 MHz): δ 12.070 (1H, s), δ 10.208 (1H, s), δ 8.138 (1H, S), δ 4.279-4.293 (2H, m), δ 2.369 (3H, s), δ 2.313 (3H, s), δ 1.331-1.360 (3H, m)

Embodiment 2: Inhibitory Effects of the Derivatives on *Eimeria tenella* of Chicken One-day-old yellow-feather fast-growing broilers were raised in a coccidia-free environment, and divided into groups for trial at the age of 18 days when no coccidian oocysts were detected by microscopy in their faeces. Weak or overweight broilers were removed, and healthy broilers were divided into 30 groups with 50 broilers in each group and weight difference between each two broilers was below 20 g. Groups 1 and 2 were respectively a control group that the broilers were neither infected nor treated, and a control group that the broilers were infected but not treated. Groups 3 to 30 were respectively administrated with different derivatives. The broilers were given ad libitum access to feed and water when the feed was added with different medicines according to Table 1 at the day the broilers were divided. 24 Hours after the trial began, 250,000 sporulated *Eimeria tenella* oocysts were inoculated via an oral gavage into the crop of every broiler in each group except group 1. Bloody stool score was measured 5 days after the inoculation and the trial was ended 7 days after the inoculation. Relative weight gain (%), survival rate (%) and the bloody stool score were evaluated.

Bloody stool score: 0, no bloody stool was observed; 1, bloody stool below 25%; 2, 25 to 50% of bloody stool; 3, 50 to 75% of bloody stool; and 4, bloody stool over 75%.

Relative weight gain (%): The broilers were weighed at the beginning and the end of the trial to calculate the average weight gain and relative weigh gain. Relative weight gain=(average weight gain of each group/average weight gain of group 1)×100%.

Deaths of the broilers: Necropsy was performed and the amount of dead broilers in each group was recorded to calculate the survival rate. Survival rate=(total amount of the broilers in each group−amount of deaths caused by coccidial infection)/total amount of the broilers in each group×100%.

Results showed that the derivatives had various inhibitory effects on *Eimeria tenella*. In view of the three parameters of survival rate, bloody stool score and relative weight gain, the derivatives IST15037, IST15043, IST15045, IST15051 and IST15031 had the highest anticoccidial activities under the same dosage (60 ppm).

TABLE 1

Inhibitory effects of the derivatives on *Eimeria tenella* of chicken

| Group | Amount | Drug | Dosage (ppm) | Survival rate (%) | Score | Relative weight gain (%) |
|---|---|---|---|---|---|---|
| 1 | 50 | — | — | 100 | 0 | 100 |
| 2 | 50 | — | — | 72 | 4 | 56.2 |
| 3 | 50 | IST15038 | 60 | 100 | 3 | 82.1 |
| 4 | 50 | IST15115 | 60 | 100 | 3 | 85.9 |
| 5 | 50 | IST15116 | 60 | 100 | 3 | 78.6 |
| 6 | 50 | IST15162 | 60 | 100 | 3 | 81.6 |
| 7 | 50 | IST15031 | 60 | 100 | 1 | 95.8 |
| 8 | 50 | IST15037 | 60 | 100 | 0 | 99.2 |
| 9 | 50 | IST15041 | 60 | 100 | 3 | 85.4 |
| 10 | 50 | IST15042 | 60 | 100 | 3 | 81.2 |
| 11 | 50 | IST15043 | 60 | 100 | 0 | 98.7 |
| 12 | 50 | IST15044 | 60 | 100 | 3 | 79.8 |
| 13 | 50 | IST15045 | 60 | 100 | 0 | 103.5 |
| 14 | 50 | IST15046 | 60 | 100 | 3 | 78.4 |
| 15 | 50 | IST15051 | 60 | 100 | 0 | 101.2 |
| 16 | 50 | IST15053 | 60 | 100 | 3 | 82.5 |
| 17 | 50 | IST15054 | 60 | 100 | 4 | 71.4 |
| 18 | 50 | IST15056 | 60 | 100 | 3 | 81.3 |
| 19 | 50 | IST15150 | 60 | 100 | 2 | 86.3 |
| 20 | 50 | IST15167 | 60 | 100 | 3 | 82.7 |
| 21 | 50 | IST15008 | 60 | 100 | 2 | 89.7 |
| 22 | 50 | IST15009 | 60 | 100 | 3 | 82.6 |
| 23 | 50 | IST15013 | 60 | 100 | 3 | 88.8 |
| 24 | 50 | IST15015 | 60 | 100 | 4 | 72.5 |
| 25 | 50 | IST15016 | 60 | 100 | 2 | 74.8 |
| 26 | 50 | IST15151 | 60 | 100 | 3 | 83.6 |
| 27 | 50 | IST15152 | 60 | 100 | 3 | 85.6 |
| 28 | 50 | IST15165 | 60 | 100 | 2 | 89.7 |

Embodiment 3: Inhibitory Effects of the Derivatives of Different Dosages on *Eimeria tenella* of Chicken One-day-old yellow-feather fast-growing broilers were raised in a coccidia-free environment, and divided into groups for trial at the age of 18 days when no coccidian oocysts were detected by microscopy in their faeces. Weak or overweight broilers were removed, and healthy broilers were divided into 16 groups with 50 broilers in each group and weight difference between each two broilers was below 20 g. Groups 1 and 2 were respectively a control group that the broilers were neither infected nor treated, and a control group that the broilers were infected but not treated. Groups 3 to 16 were respectively administrated with different kinds or different dosages of derivatives. The broilers were given ad libitum access to feed and water when the feed was added with different medicines according to Table 2 at the day the broilers were divided. 24 Hours after the trial began, 250,000 sporulated *Eimeria tenella* oocysts were inoculated via an oral gavage into the crop of every broiler in each group except group 1. Bloody stool score was measured 5 days after the inoculation and the trial was ended 7 days after the inoculation. Relative weight gain (%), survival rate (%) and the bloody stool score were evaluated (according to embodiment 2).

Results showed that the inhibitory effects of the derivatives on *Eimeria tenella* of chicken were dosage-dependent, and a high dosage had no negative effect on production of the broilers.

TABLE 2

Inhibitory effects of the derivatives of different dosages on *Eimeria tenella* of chicken

| Group | Amount | Drug | Dosage (ppm) | Survival rate (%) | Score | Relative weight gain (%) |
|---|---|---|---|---|---|---|
| 1 | 50 | — | — | 100 | 0 | 100 |
| 2 | 50 | — | — | 70 | 4 | 61.2 |
| 3 | 50 | IST15051 | 5 | 96 | 4 | 80.4 |
| 4 | 50 | IST15051 | 10 | 100 | 2 | 88.6 |
| 5 | 50 | IST15051 | 20 | 100 | 0 | 95.9 |
| 6 | 50 | IST15051 | 50 | 100 | 0 | 98.7 |
| 7 | 50 | IST15051 | 100 | 100 | 0 | 101.2 |
| 8 | 50 | IST15051 | 200 | 100 | 0 | 99.4 |
| 9 | 50 | IST15051 | 500 | 100 | 0 | 103.6 |
| 10 | 50 | IST15031 | 5 | 76 | 4 | 67.8 |
| 11 | 50 | IST15031 | 10 | 88 | 4 | 72.3 |
| 12 | 50 | IST15031 | 20 | 100 | 2 | 79.8 |
| 13 | 50 | IST15031 | 50 | 100 | 1 | 90.5 |
| 14 | 50 | IST15031 | 100 | 100 | 0 | 98.9 |
| 15 | 50 | IST15031 | 200 | 100 | 0 | 102.5 |
| 16 | 50 | IST15031 | 500 | 100 | 0 | 100.4 |

Embodiment 4: Inhibitory Effects of the Derivatives on *Eimeria acervulina* of Chicken One-day-old yellow-feather fast-growing broilers were raised in a coccidia-free environment, and divided into groups for trial at the age of 18 days when no coccidian oocysts were detected by microscopy in their faeces. Weak or overweight broilers were removed, and healthy broilers were divided into 10 groups with 50 broilers in each group and weight difference between each two broilers was below 20 g. Groups 1 and 2 were respectively a control group that the broilers were neither infected nor treated, and a control group that the broilers were infected but not treated. Groups 3 to 10 were respectively administrated with different derivatives. The broilers were given ad libitum access to feed and water when the feed was added with different medicines according to Table 3 at the day the broilers were divided. 24 Hours after the trial began, 400,000 sporulated *Eimeria acervulina* oocysts were inoculated via an oral gavage into the crop of every broiler in each group except group 1. The trial was ended 7 days after the inoculation. Relative weight gain (%), survival rate (%) and feed conversion ratio were evaluated. Results showed that the derivatives had various inhibitory effects on *Eimeria acervulina*. In view of the three parameters of survival rate, relative weight gain and feed conversion ratio, provided the same dosage (60 ppm), the derivatives IST15037, IST15043, IST15045, IST15051 and IST15031 had the highest anticoccidial activities and gave a production close to group 1.

TABLE 3

Inhibitory effects of the derivatives on *Eimeria acervulina* of chicken

| Group | Amount | Drug | Dosage (ppm) | Survival rate (%) | Relative weight gain (%) | Feed conversion ratio |
|---|---|---|---|---|---|---|
| 1 | 50 | — | — | 100 | 100 | 2.154 |
| 2 | 50 | — | — | 100 | 48.6 | 3.087 |
| 3 | 50 | IST15038 | 60 | 100 | 73.8 | 2.135 |
| 4 | 50 | IST15037 | 60 | 100 | 98.5 | 2.148 |
| 5 | 50 | IST15031 | 60 | 100 | 94.8 | 2.179 |
| 6 | 50 | IST15045 | 60 | 100 | 98.7 | 2.158 |
| 7 | 50 | IST15056 | 60 | 100 | 72.5 | 2.405 |
| 8 | 50 | IST15051 | 60 | 100 | 101.8 | 2.109 |
| 9 | 50 | IST15016 | 60 | 100 | 75.6 | 2.524 |
| 10 | 50 | IST15043 | 60 | 100 | 99.4 | 2.139 |

Embodiment 5: Inhibitory Effects of the Derivatives on *Eimeria necatrix* of Chicken One-day-old yellow-feather fast-growing broilers were raised in a coccidia-free environment, and divided into groups for trial at the age of 18 days when no coccidian oocysts were detected by microscopy in their faeces. Weak or overweight broilers were removed, and healthy broilers were divided into 10 groups with 50 broilers in each group and weight difference between each two broilers was below 20 g. Groups 1 and 2 were respectively a control group that the broilers were neither infected nor treated, and a control group that the broilers were infected but not treated. Groups 3 to 10 were respectively administrated with different derivatives. The broilers were given ad libitum access to feed and water when the feed was added with different medicines according to Table 4 at the day the broilers were divided. 24 Hours after the trial began, 100,000 sporulated *Eimeria necatrix* oocysts were inoculated via an oral gavage into the crop of every broiler in each group except group 1. Bloody stool score was measured 5 days after the inoculation and the trial was ended 7 days after the inoculation. Relative weight gain (%), survival rate (%) and the bloody stool score were evaluated (according to embodiment 2).

Results showed that the derivatives had various inhibitory effects on *Eimeria necatrix*. In view of the three parameters of survival rate, bloody stool score and relative weight gain, provided the same dosage (60 ppm), the derivatives IST15037, IST15043, IST15045, IST15051 and IST15031 had the highest anticoccidial activities and gave a production close to group 1 (Table 4).

TABLE 4

Inhibitory effects of the derivatives on *Eimeria necatrix* of chicken

| Group | Amount | Drug | Dosage (ppm) | Survival rate (%) | Score | Relative weight gain (%) |
|---|---|---|---|---|---|---|
| 1 | 50 | — | — | 100 | 0 | 100 |
| 2 | 50 | — | — | 58 | 4 | 61.4 |
| 3 | 50 | IST15038 | 60 | 100 | 2 | 79.5 |
| 4 | 50 | IST15037 | 60 | 100 | 0 | 98.9 |
| 5 | 50 | IST15031 | 60 | 100 | 1 | 92.5 |
| 6 | 50 | IST15167 | 60 | 100 | 3 | 75.8 |
| 7 | 50 | IST15008 | 60 | 100 | 3 | 81.2 |
| 8 | 50 | IST15051 | 60 | 100 | 0 | 99.5 |
| 9 | 50 | IST15045 | 60 | 100 | 0 | 102.3 |
| 10 | 50 | IST15043 | 60 | 100 | 0 | 101.5 |

The invention claimed is:

1. A derivative of 1H-imidazole-4,5-dicarboxamide having a structural formula selected from formulas (I), (II), (III) and (VI):

formula (I)

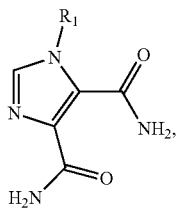

wherein R₁ is n-propyl, isopropyl, n-pentyl or n-hexyl;

formula (II)

wherein R₂ is 2-chloro-6-fluorobenzyl, 4-chlorobenzyl, 3-chlorobenzyl, 2-fluorobenzyl, 4-fluorobenzyl, 4-trifluoromethylbenzyl, 4-methylbenzyl, 4-methoxybenzyl, 2,6-dichlorobenzyl, 3,4-dichlorobenzyl, 4 nitrobenzyl, 3,5-dinitrobenzyl, 4-methanesulfonylbenzyl or 4-(4-chlorophenoxy)phenyl;

formula (III)

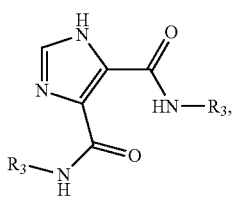

wherein R₃ is 4-methylpiperazinyl, or 4-nitrophenyl; and formula (VI)

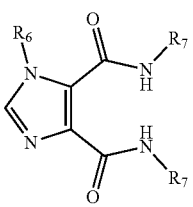

wherein R₆ is 4-chlorobenzyl, and R₇ is acetyl or propionyl.

2. A method of preparing anticoccidial drugs, comprising: utilizing the derivative of 1H-imidazole-4,5-dicarboxamide of claim 1 to prepare the anticoccidial drugs.

3. The method of claim 2, wherein the anticoccidial drugs are for a coccidia selected from the group consisting of *Eimeria tenella, Eimeria acervulina, Eimeria maxima* and *Eimeria necatrix*.

4. The method of claim 2, wherein the anticoccidial drugs are for a poultry coccidia.

5. The method of claim 4, wherein the poultry is chicken.

6. An anticoccidial drug, wherein the anticoccidial drug comprises an effective amount of the derivative of 1H-imidazole-4,5-dicarboxamide according to claim 1 as an active ingredient.

7. The anticoccidial drug according to claim 6, wherein the anticoccidial drug is a drug against poultry coccidia.

8. The anticoccidial drug according to claim 7, wherein the poultry is chicken.

9. The anticoccidial drug according to claim 6, wherein the anticoccidial drug is for a coccidia selected from the group consisting of *Eimeria tenella, Eimeria acervulina, Eimeria maxima* and *Eimeria necatrix*.

* * * * *